(12) United States Patent
Kano et al.

(10) Patent No.: US 11,773,377 B2
(45) Date of Patent: Oct. 3, 2023

(54) METHOD FOR PRODUCING EXOSOMES AND EXOSOMES OBTAINED THEREBY

(71) Applicant: TOKYO INSTITUTE OF TECHNOLOGY, Tokyo (JP)

(72) Inventors: Fumi Kano, Tokyo (JP); Masayuki Murata, Tokyo (JP); Yuki Sonoda, Tokyo (JP)

(73) Assignee: TOKYO INSTITUTE OF TECHNOLOGY, Tokyo (JP)

( * ) Notice: Subject to any disclaimer, the term of this patent is extended or adjusted under 35 U.S.C. 154(b) by 449 days.

(21) Appl. No.: 16/962,880

(22) PCT Filed: Jan. 17, 2019

(86) PCT No.: PCT/JP2019/001230
§ 371 (c)(1),
(2) Date: Jul. 17, 2020

(87) PCT Pub. No.: WO2019/142853
PCT Pub. Date: Jul. 25, 2019

(65) Prior Publication Data
US 2020/0347360 A1 Nov. 5, 2020

(30) Foreign Application Priority Data
Jan. 17, 2018 (JP) .................................. 2018-005638

(51) Int. Cl.
*C12N 5/09* (2010.01)
*A61K 9/50* (2006.01)
*C12N 15/113* (2010.01)

(52) U.S. Cl.
CPC .......... *C12N 5/0693* (2013.01); *A61K 9/5068* (2013.01); *C12N 15/113* (2013.01); *C12N 2310/141* (2013.01); *C12N 2320/32* (2013.01); *C12N 2501/998* (2013.01)

(58) Field of Classification Search
CPC ................ C12N 5/0693; C12N 15/113; C12N 2310/141; C12N 2320/32; C12N 2501/998; C12N 2500/14; C12N 5/0018; A61K 9/5068; A61K 51/02
See application file for complete search history.

(56) References Cited

FOREIGN PATENT DOCUMENTS

| CN | 108642162 A * | 10/2018 |
|---|---|---|
| EP | 3293265 A1 | 3/2018 |
| JP | 2010285426 A | 12/2010 |
| JP | 2011120520 A | 6/2011 |
| JP | 2013213688 A | 10/2013 |
| JP | 2014185090 A | 10/2014 |
| JP | 2017038566 A | 2/2017 |
| JP | 2017521644 A | 8/2017 |
| WO | WO-2005042695 A2 * | 5/2005 ............ A61K 39/12 |
| WO | 2015175856 A1 | 11/2015 |
| WO | 2016076347 A1 | 5/2016 |
| WO | 2016178532 A1 | 11/2016 |

OTHER PUBLICATIONS

Thery et al, Isolation and Characterization ofExosomes from Cell Culture Supernatantsand Biological Fluids, Apr. 1, 2006, Current Protocols in cell biology, vol. 3, issue 1, unit 3.22. (Year: 2006).*
International Search Report (and English translation) and Written Opinion for International Application No. PCT/JP2019/001230 (dated Apr. 9, 2019).
Kano et al., "Establishment and Phenotyping of Disease Model Cells Created by Cell-Resealing Technique," Scientific Reports 7(15167):1-14 (2017).
Kano et al., "A Resealed-Cell System for Analyzing Pathogenic Intracellular Events: Perturbation of Endocytic Pathways under Diabetic Conditions," PLOS One 7:e44127 (2012).
McKiernan et al., "A Novel Urine Exosome Gene Expression Assay to Predict High-Grade Prostate Cancer at Initial Biopsy," JAMA Oncol. 2(7):882-889 (2016).
Romero et al., "Intrinsic Repair Protects Cells From Pore-Forming Toxins by Microvesicle Shedding," Cell Death and Differentiation 24:798-808 (2017).
Stickney et al., "Development of Exosome Surface Display Technology in Living Human Cells," Biochemical and Biophysical Research Communications 472:53-59 (2016).
Syn et al., "Exosomes in Cancer Nanomedicine and Immunotherapy: Prospects and Challenges," Trends in Biotechnology 35(7):665-676 (2017).
Yanez-Mo et al., "Biological Properties of Extracellular Vesicles and Their Physiological Functions," Journal of Extracellular Vesicles, 4(20766):1-60 (2015).
Yim et al., "Extracellular Vesicles as Novel Carriers for Therapeutic Molecules," BMB Reports 49(11):585-586 (2016).
Yim et al., "Exosome Engineering for Efficient Intracellular Delivery of Soluble Proteins Using Optically Reversible Protein-Protein Interaction Module," Nature Communications 7(12277):1-9 (2016).
Abe et al., "Construction of Quantitative Evaluation System of Microvesicles Derived From a Living Body by Flow Cytometry," The 135th Annual Meeting of the Pharmaceutical Society of Japan, non-official translation, 26U-am10S, p. 63 (2015).
Murata et al., "Semi-Intact Cell System and Cell Resealing Technique for Image-Based Analysis of Intracellular Events: A Powerful Cellular Tool for Single Cell Biology," Seibutsu Butsuri 54(4):206-209 (2014).

* cited by examiner

*Primary Examiner* — Valarie E Bertoglio
*Assistant Examiner* — Constantina E Stavrou
(74) *Attorney, Agent, or Firm* — HESLIN ROTHENBERG FARLEY & MESITI P.C.

(57) ABSTRACT

The object of the present invention is to provide a method for incorporating an arbitrary protein, lipid, carbohydrate, or nucleic acid into an exosome. The object can be solved by a method for preparing an exosome, comprising the steps of: (a) adding a biological toxin having a perforating activity to a medium containing cells and incubating the mixture, (b) adding ATP and incubating the mixture, and (c) adding a medium containing calcium ion and incubating the mixture.

10 Claims, 4 Drawing Sheets

Western blotting analysis of exosomes derived from resealed cells

METHOD FOR PRODUCING EXOSOMES AND EXOSOMES OBTAINED THEREBY

CROSS REFERENCE TO RELATED APPLICATIONS

This application is a national stage filing under 35 U.S.C. § 371 of PCT Application No. PCT/JP2019/001230, filed on Jan. 17, 2019, which claims priority of Japanese Application No. 2018-005638, filed on Jan. 17, 2018, which is hereby incorporated by reference in its entirety.

TECHNICAL FIELD

The present invention relates to a method for preparing an exosome and an exosome obtained thereby. According to the present invention, a desired component can be contained in the exosome.

BACKGROUND ART

Microvesicles, apoptotic bodies, and exosomes are known as an extracellular vesicle which is secreted extracellularly from cells. Among these extracellular vesicles, the exosome has cell membrane-derived or endosomal membrane-derived proteins and lipids on the surface, and cytoplasm-derived nucleic acids and proteins inside. It has been reported that liposomes have a function of transmitting information between cells (Non-patent literature 1).

In addition, exosomes secreted from cancer cells or diseased cells may contain cancer-specific markers or disease-specific markers. Therefore, the development of diagnostic methods for diseases using such exosomes is underway.

CITATION LIST

Non-Patent Literature

[Non-patent literature 1] Journal of Extracellular Vesicles, (U.S.A.), 2015, vol. 4, Article: 27066
[Non-patent literature 2] JAMA Oncology (U.S.A.) 2016, vol. 2, p 882-889
[Non-patent literature 3] Trends in Biotechnology (U.S.A.) 2017, no. 7, p 665-676
[Non-patent literature 4] BMB Reports (Republic of Korea) 2016, vol. 49, p 585-586
[Non-patent literature 5] Scientific Reports (United Kingdom) 2017, vol. 7, Article number: 15167
[Non-patent literature 6] PLoS ONE (U.S.A.) 2012, vol. 7, e44127

SUMMARY OF INVENTION

Technical Problem

Further, the following methods have been reported as a technique for modifying exosomes, in order to use exosomes for drug delivery. That is, an ex vitro loading method for loading into extracellularly secreted exosomes and an in vitro loading method for removing exosomes from genetically modified cells have been reported (Non-patent literature 3). For example, as the in vitro loading method for packaging an arbitrary protein in exosomes, a method for binding an arbitrary protein to a peptide targeting the exosome membrane has been disclosed (Non-patent literature 4). However, the method disclosed in Non-patent literature 4 is a method of incorporating a protein into an exosome as a fusion protein, and thus not a method of incorporating a protein into an exosome as it is. Further, the ex vitro loading method is complicated in operation, and the loading efficiency greatly depends on the chemical properties of the substance to be loaded. Thus, it was not easy to incorporate an arbitrary protein, lipid, carbohydrate, nucleic acid, or the like into exosomes.

Therefore, the object of the present invention is to provide a method for incorporating an arbitrary protein, lipid, carbohydrate, or nucleic acid into an exosome.

Solution to Problem

The present inventors have conducted intensive studies into a method for incorporating an arbitrary protein, lipid, carbohydrate, or nucleic acid into an exosome, and as a result, surprisingly found that proteins, lipids, carbohydrates, or nucleic acids can be incorporated into exosomes by preparing exosomes using a semi-intact cell system and the cell resealing technique (referred to as a "cell resealing technique" hereafter).

The present invention is based on the above findings.

Therefore, the present invention relates to:
[1] a method for preparing an exosome, comprising the steps of: (a) adding a biological toxin having a perforating activity to a medium containing cell and incubating the mixture, (b) adding ATP and incubating the mixture, and (c) adding a medium containing calcium ion and incubating the mixture,
[2] the method for preparing an exosome according to the item [1], further comprising a step of:
(d) purifying exosomes from the medium,
[3] the method for preparing an exosome according to the item [1] or [2], wherein a cytoplasm is added in step (b),
[4] the method for preparing an exosome according to any one of the items [1] to [3], wherein the biological toxin having a perforating activity is selected from the group consisting of cholesterol-dependent cytolysin such as streptolysin O, listeriolysin O, suilysin, canilysin, equis imilysin, pneumolysin, perfringolysin O, tetanolysin O, mitilysin, human platelet aggregation factor derived from *Streptococcus mitis*, lectinolysin, pseudopneumolysin, vaginolysin, seeligeriolysin O, ivanolysin O, alveolysin O, anthrolysin O, pyolysin O, or intermedilysin; *Staphylococcus aureus* alpha toxin; and *Clostridium perfringens* theta toxin,
[5] the method for preparing an exosome according to any one of the items [1] to [4], wherein endoplasmic reticulum stress, senescence induction, hypoxic stress, radiation exposure, or cisplatin treatment is applied to the cells in step (c),
[6] the method for preparing an exosome according to any one of the items [1] to [4], wherein a foreign component is added in the step (b),
[7] the method for preparing an exosome according to any one of the items [1] to [4], wherein the foreign component is a protein, a nucleic acid, a low molecular compound, a lipid, a sugar, a fluorescent dye, a soluble polymer, or magnetic beads,
[8] an exosome obtained by the preparation method according to any one of the items [1] to [7], and
[9] an exosome comprising a fluorescent labeled molecule, provided that fluorescently labeled molecules fused to peptides targeting exosome membranes is excluded.

The cell resealing technique is known as a technique for perforating a cell membrane and introducing a specific substance into a cytoplasm (Non-patent literatures 5 and 6). It is surprising that the exosomes can be prepared from resealed cells, even though the perforation by toxins should cause a major damage on the integrity of cell membrane in resealed cells.

In the present specification, a cell obtained by the semi-intact cell resealing technique is sometimes referred to as a "resealed cell."

Advantageous Effects of Invention

According to the method for preparing an exosome of the present invention, an arbitrary protein, lipid, carbohydrate, or nucleic acid can be incorporated into an exosome. Further, many exosomes can be prepared. The exosomes obtained by the preparation method of the present invention can be used in the drug delivery.

DESCRIPTION OF EMBODIMENTS

[1] Method for Preparing an Exosome

The method for preparing an exosome comprises the steps of:
(a) adding a biological toxin having a perforating activity to a medium containing cells and incubating the mixture (hereinafter sometimes referred to as a step (a)), (b) adding ATP and incubating the mixture (hereinafter sometimes referred to as a step (b)), and (c) adding a medium containing calcium ion and incubating the mixture (hereinafter sometimes referred to as a step (c)). Further, the method for preparing an exosome may comprise the step of (d) purifying exosomes from the medium (hereinafter sometimes referred to as a step (d)).

Step (a)

In the step (a), the biological toxin having the perforating activity is added to the medium containing cells, and then the mixture is incubated. In this step, the cells are perforated by the biological toxin having the perforating activity, so as to prepare resealed cells.

Biological Toxin Having Perforating Activity

The biological toxin having the perforating activity is not limited, and there may be mentioned cholesterol-dependent cytolysin, Staphylococcal alpha toxin, and *Clostridium perfringens* theta toxin. However, cholesterol-dependent cytolysin is preferable. As the cholesterol-dependent cytolysins, there may be mentioned streptolysin O, listeriolysin O, suilysin, canilysin, equisimilysin, pneumolysin, perfringolysin O, tetanolysin O, mitilysin, human platelet aggregation factor derived from *Streptococcus mitis*, lectinolysin, pseudopneumolysin, vaginolysin, seeligeriolysin O, ivanolysin O, alveolysin O, anthrolysin O, pyolysin O, or intermedilycin, but streptolysin O, or listeriolysin O is preferable.

Perforation of cells by biological toxin having perforation activity is milder than that by surfactants etc., and the cells can be effectively resealed by calcium ion.

Cholesterol-Dependent Cytolysin

Cholesterol-dependent cytolysin uses cholesterol of the cell membrane as a receptor and can perforate cells.

For example, streptolysin O (SLO) is a cholesterol-binding bacterial toxin (protein) produced extracellularly by *Streptococcus* and has a molecular weight of 60,400. SLO selectively binds to cholesterol of the cell membrane and can form multimeric cyclic complexes to form pores of approximately 30 nm in the cell membrane. In addition, the formed pores may become as large as about 200 nm by fusion, etc. The formed pores close in a calcium ion-dependent manner. The SLO is oxygen-sensitive and thus can be deactivated by exposing it to oxygen for a long time.

The concentration of the biological toxin having the perforating activity in the medium is not particularly limited, as long as it can form pores in the cells, but is, for example, 0.001 to 1,000 µg/mL, 0.01 to 100 µg/mL, more preferably 0.05 to 10 µg/mL, most preferably 0.083 to 0.125 µg/mL. Those skilled in the art can appropriately adjust the concentration of biological toxin according to the degrees of the perforation activity and the cell toxicity of each biological toxin, and can use it.

The medium used in the step (a) is not particularly limited, and may be appropriately selected according to cells to be used. For example, the medium includes PBS, DMEM, EMEM, G-MEM, MEM alpha, Ham's F-12, Ham's F-12K, IMDM, DMEM/F12, Essential 8, HBSS, or RPMI-1640 (RPMI-1640). If serum is added to the medium, the biological toxin may be adsorbed on the serum components and the action thereof may be weakened. Therefore, a serum-free medium is preferable.

After adding the biological toxin, it is preferable to allow the mixture to stand on ice for 1 to 10 minutes. Since SLO binds to cholesterol and exhibits the perforating activity at 25° C. or more, the added SLO attaches to the cell membrane on ice without disrupting the cell membrane. Many other biological toxins are also derived from bacteria, and therefore often exhibit the perforating activity at the growth temperature of bacteria. In addition, it is preferable to bind the biological toxin such as SLO to the cell membrane on ice and then wash away the biological toxin that are not bound to cells. Then, by raising the temperature and activating biological toxin such as SLO, it is possible to prevent SLO from entering the cytoplasm through the open pores and prevent damage to intracellular organelles by SLO.

The incubation temperature by the biological toxin is not limited, but is preferably 25° C. or more, more preferably 30° C. or more, and further preferably 35° C. or more. The upper limit of the incubation temperature is not particularly limited as long as the biological toxin is not deactivated, but for example, 50° C. or less, preferably 45° C. or less, and more preferably 40° C. or less.

The incubation time is not particularly limited as long as pores are formed in the cells and there is no adverse effect on the cells, but for example, 1 to 60 minutes, preferably 2 to 30 minutes, more preferably 5 to 20 minutes, most preferably 8 to 15 minutes.

Cells used in the present invention is not particularly limited, and primary cultured cells or subcultured cells isolated from organisms can be used. The origin of cells is not particularly limited. As for mammals, there may be mentioned, for example, human, primate simian, canine, feline, swine, sheep, goat, bovine, horse, rabbit, guinea pig, rat, and mouse. As for birds, there may be mentioned chicken, quail, duck, goose, ostrich, and guinea fowl. As for reptiles, there may be mentioned gator, turtle, and skink. As for amphibians, there may be mentioned flag, and newt. As for fish, there may be mentioned tilapia, sea bream, bastard halibut, shark, and salmon. Further, as for invertebrates, there may be mentioned crab, shellfish, jellyfish, and shrimp. Furthermore, insect cells can be used. When the cholesterol-dependent cytolysin is used, cells expressing cholesterol in the cell membrane are preferable.

Step (b)

In the step (b), ATP is added and then the mixture is incubated. In this step, extracellular components are transferred into cells through the pores formed in step (a). That is to say, the extracellular fluid enters the cytoplasm, in this step.

When the medium contains calcium ion, the pores formed by the biological toxin having a perforation activity may be closed by the calcium ion. Therefore, it is preferable to add a calcium chelating agent to the medium. The chelating agent is not particularly limited, as long as it can chelate calcium, but includes EGTA (Ethylene Glycol Tetraacetic Acid), EDTA (Ethylene Diamine Tetraacetic Acid), NTA (Nitrilo Triacetic Acid), DTPA (Diethylene Triamine Pentaacetic Acid), HEDTA (Hydroxyethyl Ethylene Diamine Triacetic Acid), TTHA (Triethylene Tetramine Hexaacetic Acid), PDTA (1,3-Propanediamine Tetraacetic Acid), DPTA-OH (1,3-Diamino-2-hydroxypropane Tetraacetic Acid), HIDA (Hydroxyethyl Imino Diacetic Acid), DHEG (Dihydroxyethyl Glycine), GEDTA (Glycol Ether Diamine Tetraacetic Acid), CMGA (Dicarboxymethyl Glutamic Acid), or EDDS ((S,S)-Ethylene Diamine Disuccinic Acid).

The concentration of the calcium chelating agent is not particularly limited, as long as the effect thereof can be achieved, but is, for example, 0.1 to 5 mM, more preferably 0.5 to 3 mM.

In the step (b), a transport buffer may be added so as to increase potassium ion concentration. In addition, the calcium chelating agent may be added to the transport buffer. As the transport buffer, there may be mentioned a transport buffer having a composition of 25 mM HEPES-KOH (pH 7.4), 0.115M $CH_3COOK$, and 2.5 mM $MgCl_2$.

The concentration of the potassium ion is not particularly limited, as long as the effect of the present invention can be achieved, but is preferably 1 to 1,000 mM, more preferably 10 to 500 mM, even more preferably 50 to 300 mM.

ATP

ATP acts on mitochondrial activity, membrane fusion, membrane repair, stress response, and the like. The concentration of ATP is not limited as long as the effect of the invention can be achieved, but is preferably 0.1 to 100 mM, more preferably 0.5 to 50 mM, even more preferably 1 to 10 mM.

Foreign Component

In the present invention, a foreign component may be added to the extracellular components (extracellular fluid). The term "foreign component" as used herein means a component other than the components contained in the cytoplasm of the cells used in the method for preparing an exosome of the present invention. Thus, the foreign components include cytoplasmic components of cells other than the cells used, proteins, nucleic acids, low molecular weight compounds, lipids, sugars, fluorescent dyes, soluble polymers, or magnetic beads. As the foreign components, components to be transported by drug delivery may be added. That is, by adding proteins, nucleic acids, low-molecular compounds, lipids, sugars, or the like as components to be transported by drug delivery, it is possible to contain these components to the prepared exosomes. For example, the reseal efficiency is increased by adding cytoplasmic components. In addition, the survival rate of cells after resealing is improved. Therefore, in order to efficiently prepare exosomes, the cytoplasmic components are preferably added as the foreign components.

The molecular weight of the foreign component is not limited as long as it is incorporated into exosomes, but the upper limit is 5,000,000, preferably 500,000, more preferably 100,000, and even preferably 60,000, most preferably 3,000. The lower limit of the molecular weight is not limited, but the foreign component may be one low molecule, for example, one amino acid molecule.

As the proteins, there may be mentioned a fluorescent protein (such as GFP or DsRed, or a modified GFP or DsRed (such as Sirius, EBFP, SBP2, EBP2, Azurite, mKalamal, TagBFP, mBlueberry, mTurquoise, ECFP, Cerulean, mCerulean, TagCFP, AmCyan, mTP1, MiCy (Midoriishi Cyan), TurboGFP, CFP, AcGFP, TagGFP, AG (Azami-Green), mAG1, ZsGreen, EmGFP (Emerald), EGFP, GP2, T-Sapphire, HyPer, TagYFP, mAmetrine, EYFP, YFP, Venus, Citrine, PhiYFP, PhiYFP-m, turboYFP, ZsYellow, mBanana, mKO1, KO (Kusabira Orange), mOrange, mOrange2, mKO2, Keima570, TurboRFP, DsRed-Express, DsRed2, TagRFP, TagRFP-T, DsRed-Monomer, mApple, AsRed2, mStrawberry, TurboFP602, mRP1, Jred, KillerRed, mCherry, KeimaRed, HcRed, mRasberry, mKate2, TagFP635, mPlum, egFP650, Neptune, or mNeptune)), an antibody, a functional peptide, or a synthetic peptide.

As the nucleic acid, there may be mentioned deoxyribonucleic acid (DNA), ribonucleic acid (RNA, such as, messenger RNA, transfer RNA, or ribosomal RNA), or a functional nucleic acid (such as, miRNA, siRNA, shRNA, lincRNA, antisense RNA, antisense DNA, ribozyme, DNA enzyme, molecular beacon, riboswitch, U1 adapter, artificial chromosome, artificial DNA, or aptamer)

As the low-molecular compound, there may be mentioned, various known compounds (including peptides) registered in chemical files, or compounds obtained by combinatorial chemistry techniques (Terrett, N. K. et al., Tetrahedron, 51, 8135-8137, 1995).

As the fluorescent there may be mentioned fluorescein isothiocyanate (FITC), Oregon Green, Tokyo Green, Carboxyfluorescein, or Carboxyfluorescein diacetate.

The incubation temperature in the step (b) is not particularly limited, as long as the extracellular component can be transferred into cells, but is, for example, 4 to 50° C., preferably 15 to 45° C., more preferably 25 to 42° C., most preferably 30 to 40° C.

The incubation time is not particularly limited as long as the extracellular component can be transferred into cells, but is, for example, 1 to 120 minutes, preferably 3 to 60 minutes, more preferably 5 to 40 minutes, most preferably 10 to 30 minutes.

Step (c)

In the step (c), a medium containing calcium ion is added and then the mixture is incubated. In this step, calcium ions close the pores formed in the cells. That is, the semi-intact cells are resealed, in this step.

The calcium ion to be added is not limited, and a calcium salt can be used. Specifically, for example, $CaCl_2$ can be used. The calcium ion concentration is not particularly limited as long as the cells are resealed, but is, for example, 0.1 to 10 mM, preferably 0.2 to 5 mM, more preferably 0.3 to 2 mM.

The incubation temperature in the step (c) is not particularly limited, as long as the pores can be closed, but is, for example, 25 to 50° C., preferably 30-45° C., more preferably 35 to 40° C.

The incubation time is not particularly limited as long as the pores can be closed, but is, for example, 1 to 30 minutes, preferably 2 to 15 minutes, more preferably 3 to 10 minutes.

In the step (c), in order to relieve stress in steps (a) to (c), it is preferable to incubate at 37° C. in the presence of 5% $CO_2$ for about 2 hours. The culture temperature, $CO_2$ concentration, and culture time can be appropriately adjusted depending on the cells to be used.

Further, in the step (c), it is preferable to culture the cells for the efficient production of exosomes. For example, the culture temperature is preferably about 25 to 40° C. The culture time is preferably 1 to 96 hours, more preferably 12 to 72 hours, even more preferably 24 to 60 hours. The culture conditions such as culture temperature, culture time, and $CO_2$ concentration can be changed according to the cell type or cell state.

Furthermore, the medium used for culturing can be appropriately selected according to the cell type and the like, but it is preferable to use the serum-free medium in order to prevent contamination of exosomes derived from the bovine serum or the like.

The production amount of exosomes can be increased by applying stress to the cells during culture for the production of exosomes. In the steps (a), (b), and (c) of the preparing method of the present invention, the semi-intact cell system and cell resealing method wherein the cells are perforated, extracellular fluid flows therein, and the pores are closed (hereinafter sometimes referred to as the resealing method) is performed. The stress on the cells by the resealing method can increase the production of exosomes, compared to cells not subjected to the resealing method.

It is possible to increase the production amount of exosomes by applying other stress to the cells during the culture, in addition to the stress on the cells by the resealing method. The stress on the cells is not particularly limited, as long as the production amount of exosomes increases, for example, but includes endoplasmic reticulum stress, senescence induction, hypoxic stress, radiation exposure, or cisplatin treatment.

The endoplasmic reticulum stress (ER stress) means that proteins that have not been folded into a normal higher-order structure (denatured protein: unfolded protein) accumulate in the endoplasmic reticulum, which causes adverse effects (stress) on cells. Specifically, the endoplasmic reticulum stress can be imparted to the cells by adding tunicamycin, thapsigargin or dithiothreitol (DTT) to the medium. The additive amount of tunicamycin, thapsigargin, or dithiothreitol is not particularly limited, and can be appropriately determined according to the cell type or the like. For example, the endoplasmic reticulum stress can be imparted by adding tunicamycin to the medium at a concentration of 5 μg/mL.

The senescence induction means a stress that induces cell senescence. Specifically, the senescence can be induced by progerin expression, arrest of the cell cycle, cancerization (Ras overexpression), treatment with senescence inducers such as cisplatin, high passage number, radiation exposure, oxidative stress, ER stress, or heat shock.

The hypoxic stress means a stress caused by placing cells in a hypoxic state. Normally, in cell culture, the culture is carried out at an oxygen concentration of 20%. The hypoxic stress can be imparted to cells by culturing at an oxygen concentration of, for example, 0.05 to 5%, more preferably 0.1 to 1%. The oxygen concentration capable of imparting hypoxic stress can be appropriately changed depending on the cell type or cell state.

Step (d)

In the step (d), the exosomes purified from the medium. The exosomes are secreted into the extracellular medium by the above steps (a) to (c). In this step, the secreted exosomes are purified by a method such as concentration.

Most of the obtained particles of exosomes have a diameter of 50 to 150 nm and a density of 1.11 to 1.19 g/mL. Thus, the exosomes can be purified by utilizing such physical properties of exosomes.

Specific purification methods include ultracentrifugation, density gradient centrifugation, polymer precipitation, flow cytometer, column, or ultrafiltration.

In the ultracentrifugation, the debris of cells and the like are removed from the obtained culture supernatant by low-speed centrifugation (for example, 2,000×g). The resulting supernatant is passed through a filter of about 0.22 μm to remove microvesicles with a particle size of about 1 μm. The obtained supernatant is ultracentrifuged at 100,000×g to collect exosomes. The collected exosomes may be re-purified by ultracentrifugation at 100,000×g again.

The density gradient centrifugation may be carried out by a sucrose density gradient centrifugation method, or may be carried out by using a commercially available agent used for the density gradient centrifugation. Similar to the ultracentrifugation method, the debris of cells may be removed from the supernatant by low-speed centrifugation and the density gradient centrifugation can be performed.

In the polymer precipitation, the solubility of exosomes can be reduced to precipitate them by adding polyethylene glycol (PEG) or the like. The total exosome isolation kit, i.e. ExoQuick, which is a commercially available kit, may be used. The exosomes can be collected by mixing the liquid reagent with the sample, centrifuging at 20,000×g or less, and suspending the resulting precipitate.

In the method by flow cytometer, the exosomes are non-specifically stained using a membrane staining reagent such as PKH26, or exosome surface antigens are specifically stained by an immunofluorescence method, and then exosomes can be collected by the flow cytometer. In addition, exosomes containing FITC or fluorescent protein can be collected by the flow cytometer.

In the method by column, an ultrafiltration membrane or size exclusion chromatography column, which separates by molecular weight, can be used. Further, an affinity column in which an exosome antibody is immobilized, can be used.

In the method by ultrafiltration, the exosomes can be purified by using a filter that can separate particles of 50-150 nm. For example, by using a 0.22 μm filter, microvesicles with a particle size of about 1 μm can be removed, and exosomes with a particle size of less than 220 nm can be obtained.

[2] Exosome

The exosome of the present invention can be obtained by the method for preparing an exosome. In the exosomes obtained by the method for preparing an exosome of the present invention, the extracellular fluid flows into the cytoplasm, and thus the extracellular fluid is contained in the exosomes. Therefore, a composition thereof is different from that of exosomes obtained without using the resealing method. For example, the cell membrane is perforated by the biological toxin having the perforating activity, and therefore, some biological toxin may enter the cells and may be contained in exosomes. In addition, the expression level of CD63, the expression level of HPS70, and/or the expression level of TSG101 of the exosome of the present invention may be different from the exosome obtained without using the resealing method. Further, the exosome of the present invention may have a cholesterol content different from that of normal exosome. Furthermore, the exosome may contain the foreign component by adding the foreign component in the step (b).

Function

The exosome obtained by the preparing method of the present invention can contain the foreign component. The mechanism thereof has not been investigated in detail but is presumed as follows. However, the present invention is by no means limited to the following explanation.

For example, proteins such as HSP family and GAPDH, which are soluble in the cytoplasm, are considered to be incorporated into exosomes by diffusion. In addition, physiologically inactive substances such as dextran and BSA, which are foreign components, are also considered to be incorporated into exosomes by diffusion.

The size of pores formed by the biological toxin having the perforating activity are about 30 nm, but the pores of about 200 nm may be sometimes formed by fusion. Therefore, it is presumed that the foreign components can be introduced into the cytoplasm by diffusion and contained in exosomes, as long as the foreign components can pass through the pores.

EXAMPLE

The present invention will be described in detail hereinafter using working examples, but these working examples do not limit the scope of the present invention.

Example 1

In this example, the exosomes were prepared using HeLa cells by the preparing method of the present invention, and then the particle size distribution and the particle number thereof were measured.

HeLa cells were cultured in 10% FCS-containing D-MEM medium to 100% confluency and washed with PBS. SLO was diluted with serum-free D-MEM by a factor of 10000. 1 mL of D-MEM containing SLO (0.1 μg/mL) was added to the cells, and the cells were allowed to stand on ice for 5 minutes. After washing with PBS, 1 mL of transport buffer (25 mM HEPES-KOH (pH 7.4), 0.115M $CH_3COOK$, 2.5 mM $MgCl_2$) containing 2 mM EGTA was added, and the mixture was allowed to stand at 37° C. for 10 minutes.

Then, after washing with transport buffer, add 1 mL of L5178Y cytoplasm (1 mMATP, 1 mMGTP, Glucose (1 mg/mL), creatine kinase (0.05 mg/mL), creatine phosphate (2.62 mg/mL), sucrose (0.25M)) with protein concentration of 3 mg/mL, and the mixture was reacted at 37° C. for 20 minutes.

Then, the cells were resealed by adding $CaCl_2$ (1 mM) and incubated at 37° C. for 5 minutes. In order to relieve stress during the preparation of resealed cells, the cells were cultured for 2 hours at 37° C., in the presence of 5% $CO_2$, and then, the medium was replaced.

The cells were cultured for 12 hours at 37° C. using 5 mL of D-MEM containing 10% FCS without bovine-derived exosomes. At this time, tunicamycin (5 μg/mL) was added to the medium to impart endoplasmic reticulum stress. As a control without endoplasmic reticulum stress, the same amount of DMSO was added to the medium.

Exosomes were collected from the resulting culture supernatant by centrifugation. 5 mL of culture supernatant was centrifuged at 2,000×g for 10 minutes to remove cell debris. The resulting supernatant was filtered with a 0.22 μm filter to remove microvesicles of about 1 μm. The resulting supernatant centrifuged at 100,000×g for 70 minutes, and the supernatant was discarded. The cells were resuspended in 12 mL of PBS and centrifuged again at 100,000×g for 70 minutes. The precipitate was suspended in 50 μL of PBS to collect exosomes.

Figure 1:
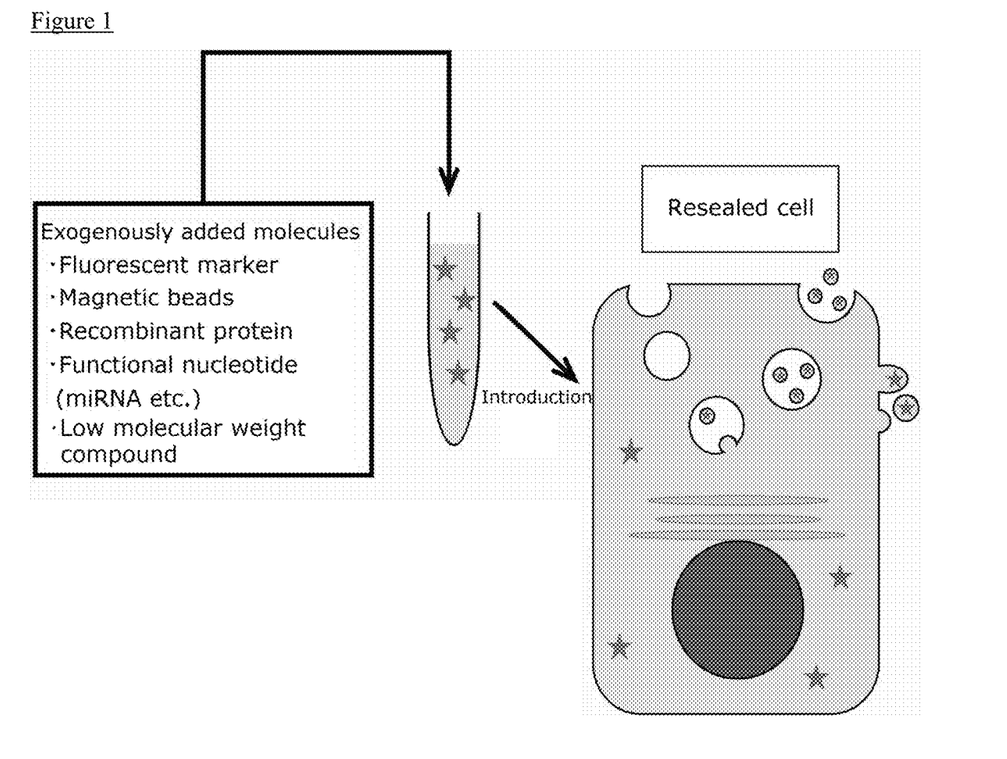
FIG. 1 is an illustration showing an outline of the method for preparing exosomes of the present invention.
Figure 2:
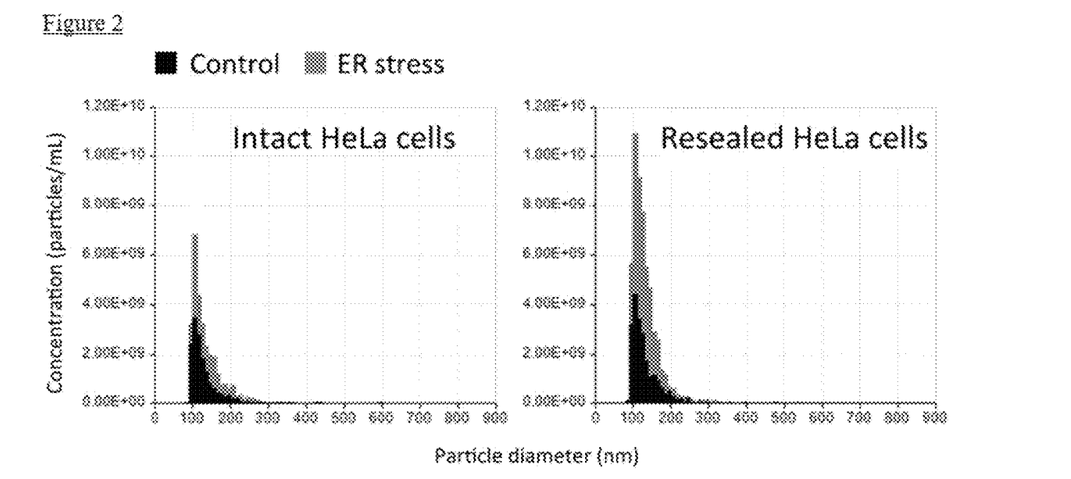
FIG. 2 is graphs showing particle size distribution and particle number of exosomes obtained from resealed cells (with or without endoplasmic reticulum stress), or particle size distribution and particle number of exosomes obtained from intact cells (with or without endoplasmic reticulum stress), using HeLa cells.

The particle size distribution and the particle number of the obtained exosomes were measured by using a nanoparticle analyzer (QNANO™, (Izon Science). The results are shown in FIG. 2.

Comparative Example 1

In this comparative example, the exosomes were prepared using HeLa cells without performing the resealing method, and then the particle size distribution and the particle number thereof were measured.

HeLa cells which were not subjected to the steps (a)-(c) of the present invention, were cultured for 12 hours at 37° C. using 1 mL of D-MEM containing 10% FCS without bovine-derived exosomes. At this time, tunicamycin (5 μg/mL) was added to the medium to impart endoplasmic reticulum stress. As a control without endoplasmic reticulum stress, the same amount of DMSO was added to the medium.

Then, exosomes were collected by centrifugation in the same manner as in Example 1. The particle size distribution and the number of particles of the obtained exosomes were measured using qNano (Izon). The results are shown in FIG. 2

As shown in FIG. 2, the number of exosomes in the ER stress-imparted group (tunicamycin added) was increased, compared to that in the control group (DMSO added), in the exosomes obtained in Example 1. That is, it was found that the ER stress causes an exosome secretion response Further, the number of exosomes obtained in Example 1 was increased compared to the number of exosomes obtained in Comparative Example 1. Therefore, it is considered that the number of exosomes is increased by the preparing method of the present invention.

Example 2 and Comparative Example 2

In this example, fluorescent labeled dextran was incorporated into exosomes, and membrane proteins were analyzed with a super-resolution microscope.

Figure 3:
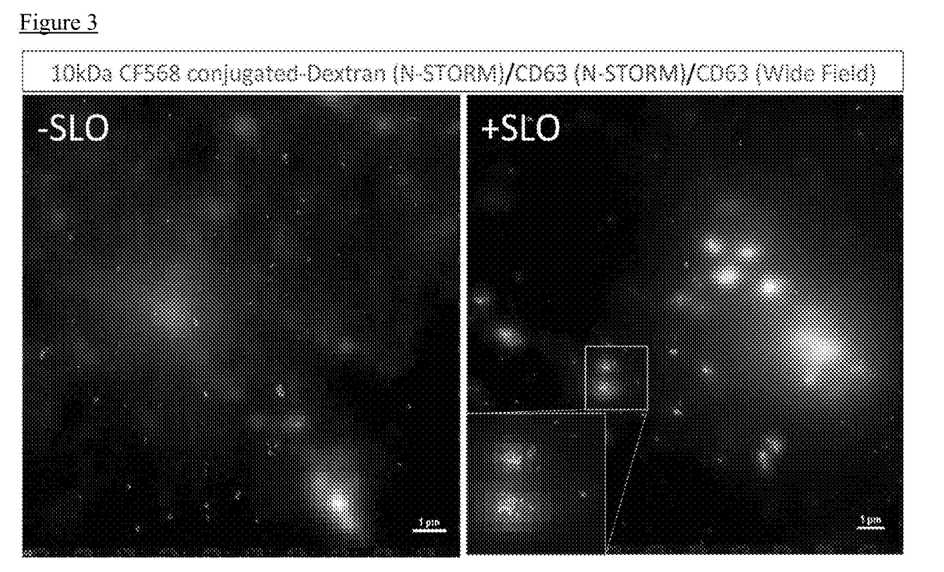
FIG. 3 is an N-STORM microscope photograph wherein CD63 of the resealed cells containing fluorescent labeled dextran is detected by an immunofluorescence method using an antibody. As a control, a microscope photograph of the intact cells is shown.
Figure 4:
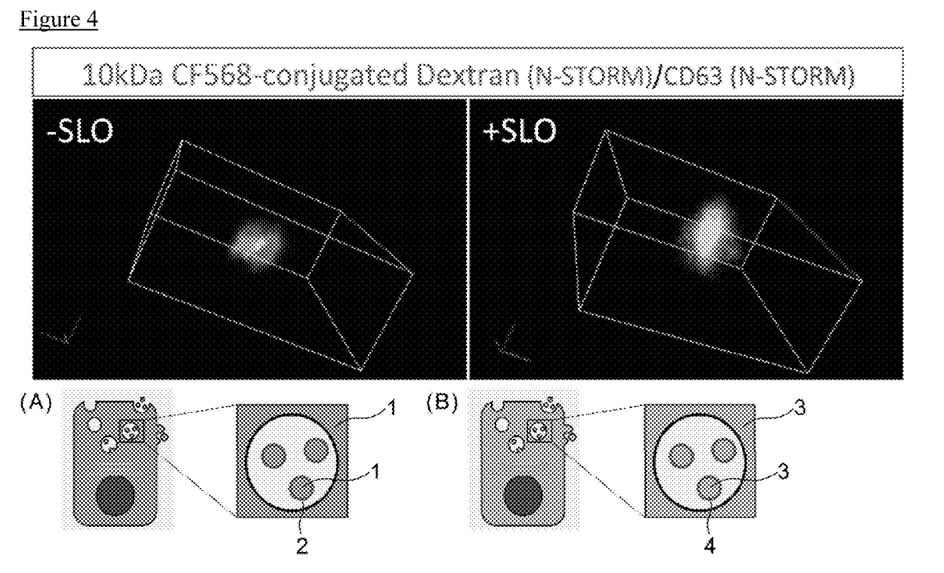
FIG. 4 is an N-STORM microscope photograph wherein CD63 of the resealed cells containing fluorescent labeled dextran is detected by an immunofluorescence method using an antibody. As a control, a microscope photograph of the intact cells is shown.

The procedure described in Example 1 was repeated, except that CF568-added dextran (molecular weight 10,000) was added to L5178Y cytoplasm, to prepare resealed cells. In order to relieve stress during the preparation of resealed cells, the cells were cultured for 2 hours at 37° C., in the presence of 5% $CO_2$. The obtained cells were fixed and subjected to the immunofluorescence method using the CD63 antibody. In Comparative Example 2, HeLa cells which were not treated with SLO, were also subjected to the immunofluorescence method using the CD63 antibody According to the observation with the super-resolution microscope, N-STORM (Nikon), it was observed that CF568-labeled dextran (10 kDa; green) was surrounded by CD63 (red) in the resealed cells. ("+SLO" in FIG. 3, (the inset photograph is an enlarged view of the square part) and "+SLO" in FIG. 4). On the other hand, in intact cells that were not treated with SLO, there was some overlap with the signal of CD63 in the vicinity of CF568-labeled dextran ("-SLO" in FIG. 4), but CF568-labeled dextran was not surrounded by CD63 ("-SLO" in FIG. 3). In resealed cells, CF568-labeled dextran present in the cytoplasm migrated into exosomes, and as a result, an image of dextran surrounded by CD63 was obtained (FIG. 4(B); "3 (green)": cytoplasm containing CF568-labeled dextran, "4 (red)": CD63). In intact cells, CF568-labeled dextran was not present in the cytoplasm, and a similar image was not observed (FIG. 4(A), "1 (blue)": cytoplasm, "2 (red)": CD63).

From these results, it was found that the cytoplasmic components were incorporated into ILV Example 3 and Comparative Example 3

In these examples and comparative examples, proteins contained in exosomes, i.e., CD63, TSG101 (ESCRT-related membrane protein), and HSP70A, were analyzed by western blotting. As a control, calnexin localized in ER was detected. Further, FITC, which is a foreign component, was analyzed by western blotting.

The procedure described in Example 1 was repeated, except that BSA labeled with FITC (BSA-FITC) was added to the L5178Y cytoplasm, and that the culture was performed in serum-free D-MEM without FBS for 48 hours, to collect exosomes. It was confirmed by fluorescence microscopy that BSA-FITC could be introduced into the cytoplasm by the resealing method ("BSA-FITC resealing cells" in FIG. 5). Further, the procedure described in Comparative Example 1 was repeated to collect exosomes.

Intact cells, resealed cells, or exosomes obtained from those cells were lysed with RIPA buffer. Then, the lysate was mixed with 6×Sample buffer, and the whole was boiled at 100° C. for 5 minutes. Subsequently, the proteins were electrophoresed and separated by SDS-PAGE. Then, the proteins in the gel were transferred to a PVDF membrane that was previously hydrophilized by semi-dry blotting. After blocking the membrane with 5% BSA, the primary antibody against exosome marker proteins, the primary antibody against calnexin (negative control), or the primary antibody against FITC was reacted, and then the secondary antibody was reacted.

Figure 5:
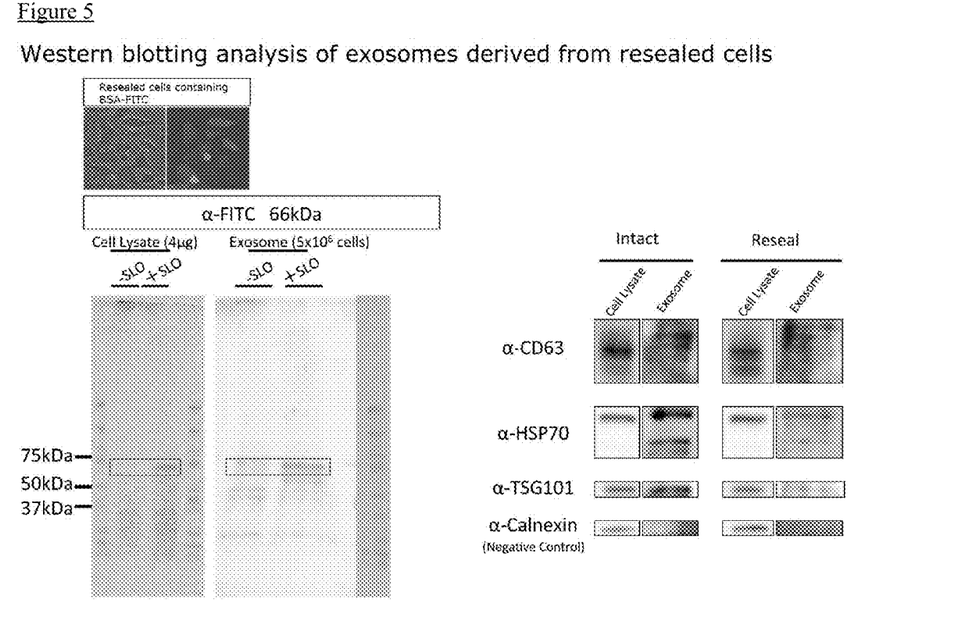
FIG. 5 is a western blotting-analyzed photograph of FITC, CD63, TSG101, and HSP70A of exosomes obtained by the preparation method of the present invention.

The target bands on the membrane were detected by using Amersham Imager 600, and as a result, as shown in FIG. 5, the BSA-FITC bands were detected only in the cell lysate and exosomes of the resealed cells (Example 3) (bands surrounded by red squares of left bottom in FIG. 5). These results indicate that BSA-FITC was taken up not only intracellularly but also into exosomes, and therefore, the exosomes wherein contents are modified in resealed cells, were secreted. Further, in the results of western blotting using antibodies against the exosome markers, exosome markers, i.e., CD63, HSP70, and TSG101, are detected from both exosomes prepared from the intact cells (Comparative Example 3) and the resealed cells (Example 3) ("α-CD63", "α-HSP70", and "α-TSG101" of right bottom in FIG. 5). Calnexin (negative control) was present in cell lysates but not in exosomes in all cases ("α-Calnexin" of right bottom in FIG. 5). Accordingly, it was confirmed that exosomes derived from resealed cells contain exosome markers like the intact cells, and that vesicles and cell debris formed by breaking the cell membrane are not the main components thereof.

Example 4 and Comparative Example 4

In this example, fluorescently labeled synthetic miRNA was incorporated into exosomes and the intracellular localization thereof was analyzed. The procedure described in Example 1 was repeated to prepare resealed cells, except that the fluorescently labeled synthetic miRNA was added with cytosol of L5178Y cells to HeLa cells, and a transport buffer containing PI (Propidium Iodide) was used. As the miRNA, AccuTarget-Fluorescein-labeled miRNA mimic (ACCUTARGE™ Negative Control #1, Bioneer, Inc.) was used. The obtained cells were observed using a fluorescence microscope. In addition, by adding PI to the transport buffer (25 mM HEPES-KOH (pH 7.4)) containing 2 mM EGTA, nucleic acids such as nuclear body were stained.

Figure 6:
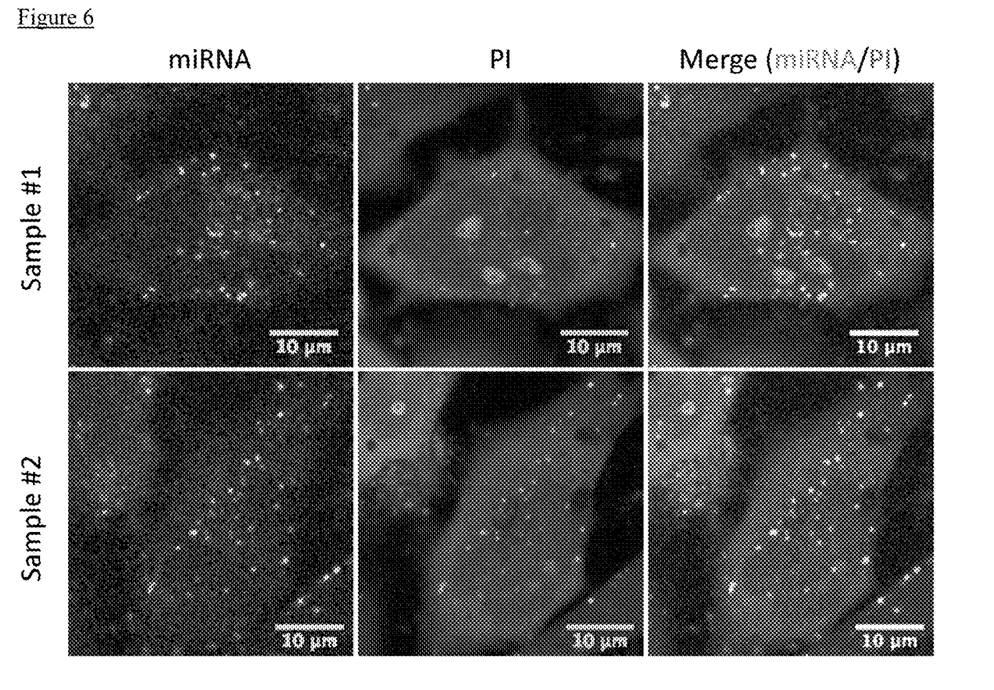
FIG. 6 is a fluorescence photograph (miRNA) of the resealed cells containing fluorescent labeled synthetic miRNA, a photograph (PI) stained by PI, and a superimposed photograph (Merge) thereof.

FIG. 6 shows a photograph of FITC fluorescence of miRNAs (shown as "miRNA"), a photograph of staining with PI (shown as "PI"), and a superimposed photograph thereof (shown as "Merge"). The localization of miRNA and the staining image of PI did not completely identical. Thus, it was suggested that miRNA might be actively accumulated in endosomes, P-body, or the like.

Next, after preparing resealed cells, the presence of miRNA in the cells and the exosome fraction was confirmed by real-time PCR. In the resealing method, synthetic cel-mir-39 mimicking nematode miRNA was added with cytosol of L5178Y cells to HeLa cells. As Comparative Example 4, the same experiment was performed using intact HeLa cells.

Figure 7:
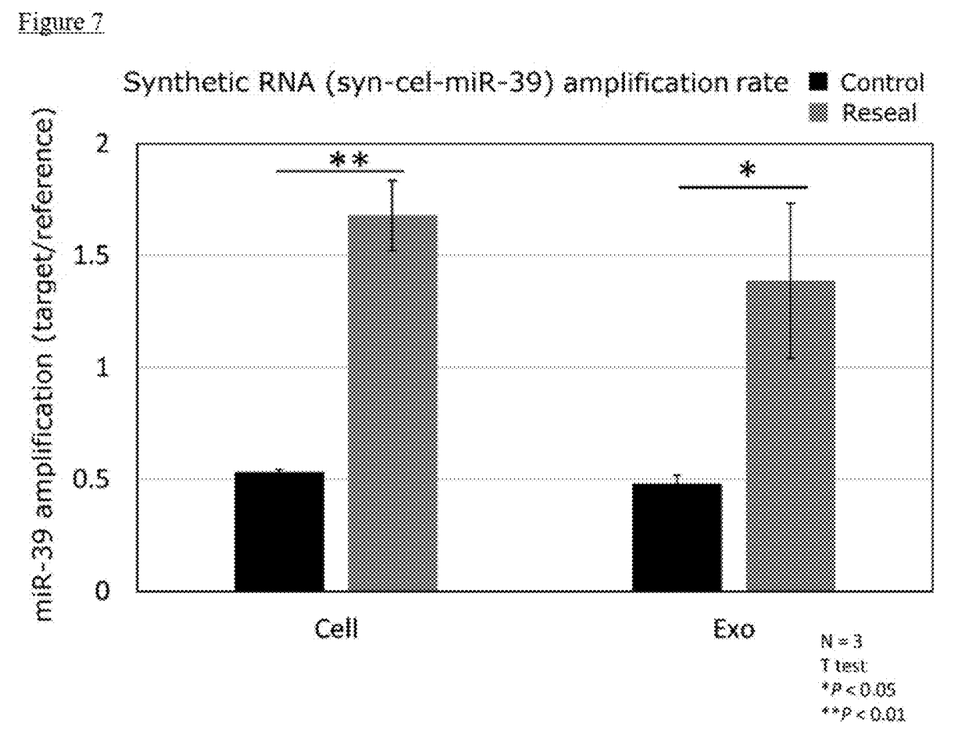
FIG. 7 is a graph showing that miRNA was introduced into cells and exosomes obtained by the method of the present invention.

As shown in FIG. 7, it was confirmed that miRNA was introduced into the resealed cells and the exosomes prepared by the method of the present invention.

INDUSTRIAL APPLICABILITY

The exosome obtained by the preparing method of the present invention can contain an arbitrary protein, lipid, carbohydrate, or nucleic acid therein. Therefore, the exosomes obtained by the preparation method of the present invention can be used in, for example, the drug delivery.

The invention claimed is:

1. A method, comprising the steps of:
   (a) adding a biological toxin having a perforating activity to a medium containing cells to form a first mixture and incubating the first mixture,
   (b) adding ATP to the first mixture to form a second mixture and incubating the second mixture, and
   (c) adding a medium containing calcium ions to the second mixture to form a third mixture and incubating the third mixture, wherein
   incubating the third mixture results in the formation of exosomes.

2. The method according to claim 1, further comprising purifying the exosomes from the third mixture.

3. The method according to claim 1, wherein step (b) further comprises adding a cytoplasm.

4. The method according to claim 1, wherein the biological toxin having a perforating activity is selected from the group consisting of cholesterol-dependent cytolysin; *Staphylococcus aureus* alpha toxin; and *Clostridium perfringens* theta toxin.

5. The method according to claim 1, wherein step (c) further comprises applying endoplasmic reticulum stress, senescence induction, hypoxic stress, radiation exposure, or cisplatin treatment to the cells.

6. The method according to claim 1, wherein step (b) further comprises adding a foreign component.

7. The method according to claim 6, wherein the foreign component is a protein, a nucleic acid, a low molecular compound, a lipid, a sugar, a fluorescent dye, a soluble polymer, or magnetic beads.

8. The method according to claim 1 wherein the biological toxin having a perforating activity comprises a cholesterol-dependent cytolysin, wherein the cholesterol-dependent cytolysin is selected from the group consisting of streptolysin O, listeriolysin O, suilysin, canilysin, equisimilysin, pneumolysin, perfringolysin O, tetanolysin O, mitilysin, human platelet aggregation factor derived from *Streptococcus mitis*, lectinolysin, pseudopneumolysin, vaginolysin, seeligeriolysin O, ivanolysin O, alveolysin O, anthrolysin O, pyolysin O, and intermedilysin.

9. The method according to claim 6 wherein the biological toxin having a perforating activity comprises a cholesterol-dependent cytolysin, wherein the cholesterol-dependent cytolysin is selected from the group consisting of streptolysin O, listeriolysin O, suilysin, canilysin, equisimilysin, pneumolysin, perfringolysin O, tetanolysin O, mitilysin, human platelet aggregation factor derived from *Streptococcus mitis*, lectinolysin, pseudopneumolysin, vaginolysin, seeligeriolysin O, ivanolysin O, alveolysin O, anthrolysin O, pyolysin O, and intermedilysin.

10. The method according to claim 7 wherein the biological toxin having a perforating activity comprises a cholesterol-dependent cytolysin, wherein the cholesterol-dependent cytolysin is selected from the group consisting of streptolysin O, listeriolysin O, suilysin, canilysin, equisimilysin, pneumolysin, perfringolysin O, tetanolysin O, mitilysin, human platelet aggregation factor derived from *Streptococcus mitis*, lectinolysin, pseudopneumolysin, vaginolysin, seeligeriolysin O, ivanolysin O, alveolysin O, anthrolysin O, pyolysin O, and intermedilysin.

* * * * *